(12) United States Patent
Unwin et al.

(10) Patent No.: US 9,855,153 B2
(45) Date of Patent: Jan. 2, 2018

(54) METHOD OF INSTALLING A PERCUTANEOUS DEVICE

(71) Applicant: Stanmore Implants Worldwide Limited, Elstree, Hertfordshire (GB)

(72) Inventors: Paul Unwin, Hertfordshire (GB); Gordon Blunn, Hertfordshire (GB)

(73) Assignee: Stanmore Implants Worldwide Limited (GB)

( * ) Notice: Subject to any disclaimer, the term of this patent is extended or adjusted under 35 U.S.C. 154(b) by 0 days.

(21) Appl. No.: 15/359,721

(22) Filed: Nov. 23, 2016

(65) Prior Publication Data

US 2017/0071763 A1 Mar. 16, 2017

Related U.S. Application Data

(62) Division of application No. 13/258,691, filed as application No. PCT/GB2010/050497 on Mar. 24, 2010, now abandoned.

(30) Foreign Application Priority Data

Mar. 24, 2009 (GB) .................................. 0905009.7

(51) Int. Cl.
*A61F 2/78* (2006.01)
*A61F 2/30* (2006.01)
(Continued)

(52) U.S. Cl.
CPC .................. *A61F 2/78* (2013.01); *A61F 2/32* (2013.01); *A61F 2/389* (2013.01); *A61F 2/40* (2013.01); *A61F 2/4603* (2013.01); *A61F 2/54* (2013.01); *A61F 2/605* (2013.01); *A61F 2/64* (2013.01); *A61F 2/30749* (2013.01); *A61F 2/38* (2013.01); *A61F 2/60* (2013.01); *A61F 2/72* (2013.01);
(Continued)

(58) Field of Classification Search
CPC ........ A61F 2002/546; A61F 2002/7887; A61F 2002/7875; A61F 2002/7881; A61F 2002/607; A61F 2002/608; A61F 2002/3674; A61F 2002/5038
See application file for complete search history.

(56) References Cited

U.S. PATENT DOCUMENTS 4,158,895 A 6/1979 Frosch et al.
4,579,558 A 1/1986 Ramer
(Continued)

FOREIGN PATENT DOCUMENTS

EP 1438937 7/2004
EP 1508317 2/2005
(Continued)

*Primary Examiner* — David Isabella
*Assistant Examiner* — Dinah Baria
(74) *Attorney, Agent, or Firm* — Andrus Intellectual Property Law, LLP (57) ABSTRACT

An intracorporeal portion of a percutaneous device for a joint disarticulation prosthesis or joint replacement prosthesis, the intracorporeal portion having an extracorporeal portion or having means for rigidly coupling directly to an extracorporeal portion, the extracorporeal portion being for location exterior to the skin, the intracorporeal portion having an articulating component for articulating with an articulating surface, wherein the articulating component is intracorporeal when installed in a human or animal subject.

19 Claims, 2 Drawing Sheets

(51) Int. Cl.

| | | |
|---|---|---|
| *A61F 2/32* | (2006.01) | |
| *A61F 2/40* | (2006.01) | |
| *A61F 2/46* | (2006.01) | |
| *A61F 2/54* | (2006.01) | |
| *A61F 2/64* | (2006.01) | |
| *A61F 2/38* | (2006.01) | |
| *A61F 2/60* | (2006.01) | |
| *A61F 2/72* | (2006.01) | |

(52) U.S. Cl.
CPC ............ *A61F 2002/30649* (2013.01); *A61F 2002/4619* (2013.01); *A61F 2002/7887* (2013.01)

(56) References Cited

U.S. PATENT DOCUMENTS

| | | |
|---|---|---|
| 4,676,799 A | 6/1987 | Legrand |
| 6,447,550 B1 | 9/2002 | Hunter et al. |
| 7,014,661 B2 | 3/2006 | Blunn et al. |
| 2003/0050704 A1 | 3/2003 | Keynan |
| 2003/0171825 A1 | 9/2003 | Blunn et al. |
| 2007/0150070 A1 | 6/2007 | Kim et al. |
| 2007/0162150 A1 | 7/2007 | Fago et al. |
| 2008/0288087 A1 | 11/2008 | Bachus et al. |

FOREIGN PATENT DOCUMENTS

| | | |
|---|---|---|
| GB | 2445869 | 7/2008 |
| WO | 89/10730 | 11/1989 |
| WO | 2003/065938 | 8/2003 |

METHOD OF INSTALLING A PERCUTANEOUS DEVICE

CROSS REFERENCE TO RELATED APPLICATION

This application is a divisional application of prior U.S. patent application Ser. No. 13/258,691, filed on Sep. 22, 2011, which is incorporated herein by reference.

FIELD OF THE INVENTION

The present invention relates to an intracorporeal portion or intracorporeal component for a percutaneous device for use in a joint disarticulation prosthesis or a joint replacement prosthesis, including shoulder or hip disarticulation prostheses.

BACKGROUND TO THE INVENTION

Disarticulation is the amputation of a limb through a joint. Often, disarticulation occurs without the cutting of bone. For example, hip disarticulation is an amputation through the hip joint, removing the entire leg at the hip joint. Shoulder disarticulation is an amputation through the shoulder joint, removing the entire arm at the shoulder joint. Disarticulation is also known as exarticulation.

Amputees who have undergone either disarticulation often wish to be fitted with prosthetic equipment that will allow them to replicate at least a portion of the function of the missing limb.

Unlike in a transhumeral amputation or transfemoral amputation, where the shoulder and hip are left intact and the patient has a humeral/femoral stump to attach an external prosthesis to, in a shoulder or hip disarticulation the patient has no residual limb stump extending from the scapula or pelvis to be received in the socket of an external prosthesis (exoprosthesis) and to provide a stable anchoring point for the prosthesis. In a shoulder or hip disarticulation the prosthesis must somehow be secured around the patient's pelvis/scapula. It is therefore difficult and cumbersome to reliably secure shoulder/hip disarticulation prostheses to patients.

For a hip disarticulation prosthesis, an exoprothesis having a hip joint, a knee joint, and an ankle joint should be provided. Typically a prosthetic device for hip disarticulation would have a large socket that receives and is affixed to the lower portion of the torso of the amputee, the socket being strapped around the patient's body. An example of a hip disarticulation prosthesis is described in U.S. Pat. No. 7,153,329 (Wilson). For a shoulder disarticulation prosthesis, an exoprosthesis having a shoulder joint, elbow joint and wrist joint should be provided. Typically a prosthetic device for a shoulder disarticulation would have a large socket that receives and is affixed to the shoulder area and is secured by strapping the socket around the patient's torso.

Such hip and shoulder disarticulation prostheses are uncomfortable to wear and use and suffer from numerous problems at the skin-socket interface. Focal points of increased stress caused by non-uniform pressure distribution can lead to skin-related complications, whilst the unnatural microbial environment generated in the socket is detrimental to the maintenance of healthy tissues. Furthermore, disarticulation exoprostheses are difficult to secure to a patient and can be unstable.

Even in transhumeral or transfemoral amputation, where the patient has a humeral or femoral stump to attach an external jointed limb prosthesis to, the patient will still have difficulty using the prosthesis as it is difficult for the patient to control and move the joint(s) of the external prosthesis.

Most jointed exoprostheses fall into two categories, these being body-powered prostheses and motor-actuated/myoelectric prostheses. A body-powered prosthesis is powered and controlled by gross body movements. For a prosthetic arm with an elbow joint and/or a gripping element (often a hook), these movements, usually of the shoulder, upper arm, or chest are captured by a harness system, which is attached to a cable that is connected to the exprosthesis, to control the prosthesis joint(s). However, such body-powered prostheses are not cosmetically pleasing and are difficult to control.

The myoelectric prosthesis is an external prosthesis that is linked to the residual musculature through an external electrode placed on the skin. These electrodes pick up the faint electrical signal produced by voluntary contractions of the residual muscles. This activates an electrically powered external prosthesis. However, the link is crude and the movements which can be produced are therefore relatively crude. Such prostheses are also heavy and difficult to use.

SUMMARY OF INVENTION

According to a first aspect of the invention, there is provided an intracorporeal portion of a percutaneous device for a joint disarticulation prosthesis or joint replacement prosthesis, the intracorporeal portion having an extracorporeal portion or having means for rigidly coupling directly to an extracorporeal portion, the extracorporeal portion being for location exterior to the skin, the intracorporeal portion having an articulating component for articulating with an articulating surface, wherein the articulating component is intracorporeal when installed in a human or animal subject.

The intracorporeal portion of the present invention can be used as part of a joint disarticulation prosthesis, for a subject that has had a joint disarticulation. A device incorporating the intracorporeal portion provides a prosthesis that does not have the problems associated with the skin-socket interfaces of prior art disarticulation prostheses. By providing the intracorporeal portion with an articulating component, the intracorporeal portion can articulate with a corresponding articulating surface, and the intracorporeal portion therefore replaces part of the subject's joint. The articulating component of the device effectively forms one component of a joint, the articulating surface forming the other component of the joint. Suitably, at least a portion of the extracorporeal component is located exterior to the skin when installed in a subject. Suitably, at least a portion of the extracorporeal component passes through the skin when installed in a subject.

The intracorporeal portion of the present invention can also be used as part of a joint replacement prosthesis, for a subject that has had a partial limb amputation and requires a joint replacement prosthesis. The term joint replacement prosthesis refers to a prosthesis for replacing a subject's joint. Joint replacement prostheses can be partial (replacing part of a subject's joint) or total (replacing the whole a subject's joint). Joint replacement prostheses may be inside the body (endoprostheses) or external (exoprostheses). By providing the intracorporeal portion with an articulating component, the intracorporeal portion can articulate with a corresponding articulating surface, and the intracorporeal portion therefore replaces part of the subject's joint. Muscle from the subject's residual limb can be attached to the intracorporeal portion of the percutaneous device when it is installed in the subject. This provides a direct link between the subject's musculature and the percutaneous device, and allows the subject to move the percutaneous device using their own residual muscles. The extracorporeal portion of the percutaneous device can have means for attaching an exoprosthesis, therefore the patient can move the exoprosthesis by using their muscles, attached to the intracorporeal portion of the percutaneous device, to move the percutaneous device. This device provides a means for replacing a joint in a subject that has had a limb amputation wherein the device does not suffer from the problems of prior art body-powered or myoelectric jointed exoprostheses, such as difficulty in control of movement at the joint.

The term subject or patient as used herein refers to a human or animal subject.

The articulating component can articulate with the articulating surface directly, or via a prosthetic bearing surface.

Percutaneous devices are devices that penetrate the skin of a human or animal body. Osseointegrated percutaneous devices are known in the prior art, for example for providing secure means of attaching an external prosthesis to the bone within a limb stump without the use of bulky and inconvenient braces, straps or sockets. WO 01/97718 (University College London) discloses an osseointegrated percutaneous prosthesis comprising a first component shaped for implantation into bone of a limb stump, a second component for location between the bone and the skin and a third component for location exterior to the skin. None of the osseointegrated devices of the prior art provide means for securing a prosthetic limb to a subject which has undergone a joint disarticulation or wherein the subject does not have a residual limb stump (i.e. a residual femoral or humeral stump) to which an osseointegration device can be implanted (for example, by implantation into the intramedullary cavity of bone in the stump).

According to a second aspect of the invention there is provided a percutaneous device of or for a shoulder or hip joint disarticulation prosthesis, the percutaneous device comprising an intracorporeal portion and an extracorporeal portion for location exterior to the skin, the percutaneous device further comprising an articulating component, the articulating component comprising a ball or socket component. Preferably the articulating component is intracorporeal when installed in a human or animal subject. In other words, the articulating surface is located inside the body in use.

The natural shoulder and hip joint are ball and socket joints, wherein a ball of one bone is received in a cavity or socket of another, allowing some degree of rotary motion in every direction. Suitably the percutaneous device is used as a shoulder or hip disarticulation prosthesis, or as part of a shoulder or hip disarticulation prosthesis, and provides a prosthesis that does not have the problems associated with the skin-socket interfaces of prior art disarticulation prostheses. By providing the percutaneous device with an articulating component which is either a ball or socket component, the percutaneous device can articulate with a corresponding socket or ball in use, as appropriate, and the percutaneous device thereby replaces part of a subject's shoulder or hip joint.

Preferred features of the first and second aspects of the invention are described below.

Preferably the articulating component is intracorporeal when installed in a human or animal subject. Preferably the articulating surface is intracorporeal in use.

Preferably the articulating component is integral with or rigidly coupled to the intracorporeal portion or the extracorporeal portion of the percutaneous device in use. The articulating component is therefore non-movable relative to the intracorporeal portion or extracoroporeal portion of the device. Preferably the intracorporeal portion has a body component, the articulating component being integral with or coupled to the body component in use.

Preferably the articulating component comprises a ball component or a socket component and the device articulates with an articulating surface of a ball and socket joint, when implanted. Suitably the device may be for use as part of a shoulder or hip disarticuation prosthesis.

Preferably the device is adapted for use in an anatomical shoulder prosthesis or anatomical hip prosthesis. In an anatomical shoulder or hip prosthesis, the component that replaces the proximal end of the humerus or femur has a ball component, which articulates with a socket in the scapula or pelvis (which may be a natural socket or a replacement socket shell). Preferably the articulating component is a ball component, the ball component being intracorporeal when installed in a human or animal subject. Preferably the ball component is comprised as part of the intracorporeal portion of a percutaneous device, such that the ball component is within the body of a subject when installed.

Preferably the articulating component articulates with an articulating surface of a hinge joint when implanted in a subject. Hinge joints in the human body can be found, inter alia, at the knee, elbow and ankle. The articulating component could of course articulate with an articulating surface of joints, other than ball-and-socket or hinge type joints.

Preferably the articulating component articulates with a natural articulating surface of a subject's joint in use. Suitably, in use, the articulating component can articulate with the articulating surface directly or via a prosthetic bearing surface. For example, the articulating component may be adapted (i.e. sized and shaped) to articulate with an articulating surface of a patient's hip joint.

Preferably the intracorporeal portion comprises a proximal end and a distal end, the articulating component being located at the proximal end of the intracorporeal portion when installed in a subject. In this context the term proximal means located near or towards the centre of the subject's body or limb when the device is installed and distal means located away from the centre of the body or limb when the device is installed.

Preferably the articulating surface is a hip socket or a shoulder socket of a subject, or is a prosthetic bearing surface installed in a hip socket or shoulder socket of a subject in use. For example, for a hip disarticulation, the articulating component may be a ball component that may articulate with a prosthetic socket liner such as a prosthetic acetabular shell or cup. The percutaneous device is able to pivot relative to the subject's pelvis/scapula, and provides a stable means for coupling an external limb prosthesis to the subject and for transmitting the load from the external limb prosthesis through the subject's bone, rather than through the subject's soft tissues. Unlike in prior art percutaneous devices for attachment of external limb prostheses, the intracorporeal portion of this aspect of the invention is not osseointegrated, and hence the percutaneous device can be pivoted relative the subject's bone, allowing replication of the action of the patient's joint. The present invention therefore provides a means for coupling an external limb prosthesis to a subject's skeleton, via an articulating joint, without rigidly fixing the percutaneous prosthesis to the subject's bone.

Preferably the articulating surface is a condylar surface of a subject's knee joint and the articulating component is a corresponding tibial hinge component for articulating with the condylar surface. Suitably the tibial component of the percutaneous device is adapted to articulate with the condylar surface of a subject's knee joint, for use in a knee joint disarticulation prosthesis.

Preferably the articulating component articulates with a prosthetic articulating surface in use. Suitably, the articulating surface is prosthetic, having been implanted in the subject's body. Preferably, the articulating surface is a prosthetic articulating surface of an endoprosthesis.

Preferably the articulating component comprises a socket component, the socket component articulating with a ball component of a bone anchored endoprosthesis in use. In this context, the term endoprosthesis is used to refer to a prosthesis that is installed in a subject's body internally and the term exoprosthesis is used to refer to a prosthesis that is applied externally to a subject's body. The socket component of the percutaneous device can, for example, articulate with a ball component of a bone anchored glenoid prosthesis when used for a shoulder disarticulation prosthesis. The percutaneous device is therefore able to pivot relative to the subject's pelvis/scapula as appropriate, and provides a stable means for coupling an external limb prosthesis to the subject and transmitting the load from the external limb prosthesis through the subject's bone, rather than through the subject's soft tissues. Unlike in prior art percutaneous devices for attachment of external limb prostheses, the percutaneous device of this preferred aspect of the invention is not osseointegrated, and hence the percutaneous device can pivot relative the subject's bone, allowing replication of the action of the patient's hip or shoulder joint. The present preferred aspect of the invention therefore provides a means for coupling an external limb prosthesis to a subject's skeleton, via an articulating joint, without rigidly fixing the percutaneous prosthesis to the subject's bone. The percutaneous device couples to a bone anchored device having a ball component for articulating with the socket component of the percutaneous device, providing a reverse anatomical joint configuration.

Preferably the articulating component comprises a tibial component for articulating with a femoral hinge component of a knee endoprosthesis. Suitably, the tibial component can articulate with a condylar surface of a femoral hinge component of an implanted endoprosthesis, the intracoporeal component forming part of a joint replacement prosthesis for implantation in a subject that has undergone a transfemoral amputation. The intracoporeal component is therefore able to pivot relative to the subject's femur, to provide a knee joint within the subject's femoral stump. Similarly the articulating component could be adapted (i.e. sized and shaped) to articulate with a corresponding joint component of an elbow joint of an implanted endoprosthesis, the percutaneous device forming part of a joint replacement prosthesis for implantation in a subject that has undergone a transhemoral amputation. The percutaneous device is therefore able to pivot relative to the subject's elbow, to provide an elbow joint within the subject's humoral stump. Suitably, residual muscles at the site of the limb amputation can be secured to the intracoporeal component when it is installed, anchoring muscle to the intracoporeal component and therefore allowing the subject to control movement of the intracoporeal component/percutaneous device using their residual muscle at the limb stump.

According to a third aspect of the invention there is provided a kit for a joint disarticulation prosthesis or joint replacement prosthesis, the kit comprising an intracorporeal portion or percutaneous device according to the first or second aspect of the invention and an endoprosthesis having an articulating surface for articulating with the articulating component. Suitably the endoprosthesis has a proximal end and a distal end, the articulating surface being at the distal end of the endoprosthesis when implanted. Suitably the endoprosthesis has bone anchoring means for rigidly attaching the endoprosthesis to a subject's bone in use. The bone anchoring means may be a stem for engagement in a resected long bone. Preferably the endoprosthesis has a ball component and bone anchoring means for rigidly attaching the endoprosthesis to bone in use. Preferably the endoprosthesis has a body portion for mounting into bone, the body portion having a substantially frustoconical taper with an integral screw formation extending terminally therefrom whereby when the endoprosthesis is fixed in place to bone by the screw formation, the taper of the body assists in stabilising the endoprosthesis.

Suitably the device may be adapted for use in a reverse anatomical shoulder prosthesis or a reverse anatomical hip prosthesis. In certain circumstances it is desirable to reverse the natural anatomical configuration of the joint, whereby in a reverse anatomical joint the socket component of the joint is present on the proximal humeral/femoral component and articulates with a ball component secured to the scapula/pelvis. Reverse anatomical configuration would be useful in particular for use in shoulder joint disarticulations where the subject's shoulder socket requires replacement, and wherein it may be difficult to implant an anatomical glenoid shell that is large enough to stabilize the humeral prosthesis and prevent proximal migration.

Preferably the percutaneous device has bone anchoring means for rigidly anchoring the device or at least part of the device to bone in use. Preferably the articulating component is extracorporeal when installed in a subject. Preferably the articulating component is located at a distal end of the extracorporeal portion when installed. Preferably the bone anchoring means comprises a screw formation extending from the proximal end of the percutaneous device when installed. Preferably the bone anchoring means further comprises a substantially frustoconical taper, the screw formation extending terminally from the frustroconical taper, whereby when the prosthesis is bone anchored by the screw formation, the taper assists in stabilising the percutaneous device. Preferably the articulating component is a ball component. Preferably the ball component is comprised as part of the extracorporeal portion of the percutaneous device, such that the ball component is outside the body of a subject when installed. Preferably the ball component is located at the distal end of the extracorporeal portion when installed. Preferably the ball component articulates with a socket of an exoprosthetic device in use. The ball component of the percutaneous device therefore provides a stable, bone anchored support for coupling an external limb prosthesis to a subject's skeleton, via an articulating ball and socket joint.

With regard to the first, second and third aspects of the invention, when the articulating component is a ball component, the ball component is preferably substantially spherical. The ball component is preferably a rounded, convex articulating surface.

Preferably the intracorporeal portion or percutaneous device further comprises a flange extending outwardly from the intracorporeal portion in use. The flange provides a large surface area for integration with skin and fibrous tissue. Preferably the flange is non-circular in shape in the plane transverse to the longitudinal axis of the intracorporeal portion. The non-circular flange or enlarged distal portion provides rotational stability to a socket of an exoprosthesis installed on the stump and prevents spinning of the socket on the stump (when the intracorporeal portion is not coupled to the extracorporeal portion, the intracorporeal portion being implanted fully under a patient's skin). For example, the non-circular flange or enlarged distal portion may be oval shaped.

Preferably at least a portion of the intracorporeal portion is porous. Advantageously, high porosity zones enhance tissue ingrowth (skin and/or muscle tissue), whilst the less porous zone maintains strength characteristics of the intracorporeal portion.

Preferably the intracorporeal portion has a plurality of apertures for attaching a subject's soft tissue to the intracorporeal portion. Preferably the apertures comprise throughholes. Preferably the diameter of each aperture is around 1 to 2 mm. These macro-sized apertures are suitably large enough to allow a needle and polymer suture material (such as Fiberwire(®)) to pass through, such that muscle can be secured to the flange using sutures. The sutures may be permanent or temporary. After implantation, over time, muscle tissue can ingrow through the macro-sized apertures, further securing the device to the nearby tissue.

Preferably the intracorporeal portion and extracorporeal portion are separate pieces, and are rigidly coupled together in use. Suitably, where the intracorporeal portion and extracorporeal portion are separate pieces, at least a portion of the extracorporeal portion is located exterior to the skin when installed in a subject. Preferably the extracorporeal portion has a male pin and the intracorporeal portion has a corresponding female socket for receiving the male pin of the extracorporeal portion. This allows the intracorporeal and extracorporeal portions to be coupled together. Preferably the device has means for securely coupling the intracorporeal and extracorporeal portions together, releasably or non-releasably. Alternatively, the intracorporeal portion and extracorporeal portion are integral, forming a single piece percutaneous device.

Preferably at least a portion of the intracorporeal portion is treated to promote cutaneous and/or muscle integration. Preferably at least a portion of the intracorporeal portion has a surface coating to promote cutaneous integration.

According to a fourth aspect of the invention there is provided a percutaneous device comprising an intracorporeal portion according to the first or third aspect of the invention, the percutaneous device further comprising an extracorporeal component for location exterior to the skin, the extracorporeal component being integral with or coupled to the intracorporeal component in use. The extracorporeal component may have any of the preferred features explained above.

According to a fifth aspect of the invention there is provided a joint disarticulation prosthesis or joint replacement prosthesis including an intracorporeal portion or percutaneous device according to the previously described aspects of the invention. Preferably there is provided a shoulder or hip disarticulation prosthesis including a percutaneous device according to the previous described aspects of the invention.

According to a sixth aspect of the invention there is provided an intracorporeal component for a percutaneous device, the intracorporeal component having means for attachment to a bone, the intracorporeal component being adapted for being implanted fully subcutaneously such that no portion of the intracorporeal component extends through the skin when implanted in a subject, the intracorporeal component having a female socket for receiving a corresponding male pin of an extracorporeal component, the extracorporeal component being for location exterior to the skin. The female socket and male pin provided allow for coupling of the extracorporeal component to the intracorporeal component if desired. Suitably, a portion of the extracorporeal component is located exterior to the skin when installed. The intracorporeal component will be fully under the skin when implanted. If the extracorporeal component is not installed in the intracorporeal component, the female component of the intracorporeal component will be fully covered by skin.

This differs from prior art systems, such as that disclosed in U.S. Pat. No. 4,158,895 (Reswick), wherein the distal end of the intracorporeal support extends through the skin when implanted, such that the female socket for attachment of the extracorporeal component is exposed and the pin of the extracorporeal component can be coupled to the intracorporeal support without further medical intervention to expose the female socket. By implanting the intracorporeal component such that it is fully under the skin, with no part of it extending through the skin, the intracorporeal component can be left in the patient indefinitely as a stump extender. The intracorporeal component can have a distal flange or enlarged distal portion that extends outwardly from the intracorporeal component in use, the flange or enlarged distal portion being non-circular in shape in the plane transverse to the longitudinal axis of the intracorporeal component. The non-circular flange or enlarged distal portion is also adapted for being implanted fully subcutaneously, such that no portion of the intracorporeal component extends through the skin when implanted. The non-circular flange or enlarged distal portion provides rotational stability to a socket of an exoprosthesis installed on the stump and prevents spinning of the socket on the stump. For example, the non-circular flange or enlarged distal portion may be oval shaped. The means for attachment to a bone can be any suitable means for rigidly attaching the device to a bone; for example, it may be a stem for insertion into an intramedullary cavity of a bone stump, or may be a collar that can rigidly receive a bone stump therewithin.

According to a further aspect of the invention there is provided a kit for a percutaneous device, the kit comprising an intracorporeal component according to the sixth aspect of the invention, the kit further comprising an intracorporeal plug receivable in the female socket of the intracorporeal component, the plug being fully intracorporeal when installed. Suitably, the plug is adapted to be fully subcutaneously installed, such that no portion of the plug extends through the skin when implanted.

According to a further aspect of the invention there is provided a percutaneous device, the device comprising an intracorporeal component according to the sixth aspect of the invention and an extracorporeal component for location exterior to the skin, the extracorporeal component having a male pin receivable in the female socket of the intracorporeal component for rigidly coupling the extracorporeal component to the intracorporeal component.

According to a further aspect of the invention there is provided an intracorporeal component for a percutaneous device, the intracorporeal component having means for attachment to a bone, the device further comprising a flange extending outwardly from the intracorporeal component in use, the flange being non-circular in shape in the plane transverse to the longitudinal axis of the intracorporeal component. The non-circular flange or enlarged distal portion provides rotational stability to a socket of an exoprosthesis installed on the stump and prevents spinning of the socket on the stump. The flange may be an enlarged distal portion that extends outwardly from the intracorporeal component. The longitudinal axis of the intracorporeal component is the axis parallel with the axis of implantation of the component in a subject. The flange may be oval in cross-sectional shape for example.

According to a further aspect of the invention there is provided a method of installing in a subject an intracorporeal portion or percutaneous device for a joint disarticulation prosthesis or joint replacement prosthesis as described in the first or second aspects of the invention, the method comprising the steps of
(i) implanting the intracorporeal portion under the skin;
(ii) coupling the articulating component with the articulating surface such that the articulating component can articulate with the articulating surface in use.

BRIEF DESCRIPTION OF THE DRAWINGS

A preferred embodiment of the present invention will now be more particularly described by way of example only with reference to the accompanying drawings, wherein.

DESCRIPTION OF THE PREFERRED EMBODIMENTS

The present embodiments represent currently the best ways known to the applicant of putting the invention into practice. But they are not the only ways in which this can be achieved. They are illustrated, and they will now be described, by way of example only.

Figure 1:
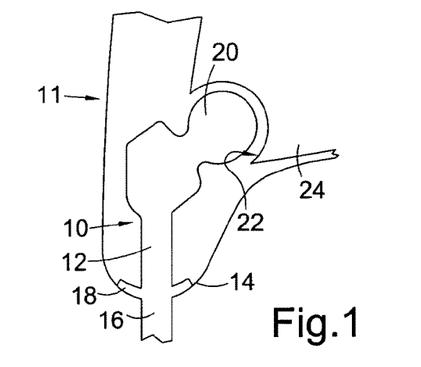
FIG. 1 shows a diagrammatic part cross-section through an embodiment of a percutaneous device for use in an anatomical hip disarticulation prosthesis, the device shown installed in a subject, the device having a ball component received in a subject's hip socket.

Referring to FIG. 1, this shows a percutaneous device 10 installed in a subject 11. The percutaneous device 10 has an intracorporeal or subcutaneous portion 12 which resides under the skin 14 when the device is installed and an extracorporeal or external portion 16 which extends from the skin when the device is installed. The device may be made up from separate components connected together, or the components may be formed integrally.

In FIG. 1, the percutaneous device 10 is shown installed at the subject's hip. The device 10 has a ball component 20 at its proximal end when installed which is received in and articulates with the subject's natural hip socket (the acetabulum) 22 in the subject's pelvis 24. Alternatively the ball component 20 may be received in and articulate with an artificial liner in the subject's hip socket, such as a prosthetic acetabular shell (not shown in the figures). The ball component is a substantially spherical, convex, articulating surface that is able to articulate with a subject's natural or prosthetic hip socket.

Percutaneous devices with ball components of a range of different sizes can be provided to allow for differences between patients. Alternatively, the ball component may be provided as a separate component from the body of the intracorporeal portion 12 of the device, for assembly together before installation in a subject. In this way, the ball component may be provided as a modular component for use with a single percutaneous device body, and the desired ball size can be selected and assembled to the percutaneous device body.

The percutaneous device 10 has a flange or flange assembly 18, extending outwardly from the longitudinal axis of the intracorporeal portion 12. The flange 18 may be integral with the body of the intracorporeal portion 12, or may be a separate piece which is attached to the intracorporeal portion 12. The flange assembly provides a large surface area for integration with skin and fibrous tissue. The percutaneous device may be installed in a one-stage procedure or in a two-stage procedure wherein the intracorporeal portion 12 of the device 10 is installed first and allowed to integrate before the flange 18 and extracorporeal portion 16 are attached. Alternatively, the intracorporeal portion 12 and flange 18 can be is installed first and allowed to integrate before the extracorporeal portion is attached. The flange is curved in shape, the surface of the distal portion being convexly curved and the surface of the proximal portion being concavely curved. This helps to prevent stresses being applied to the soft tissues that lie over the peripheral edge of the flange assembly.

The percutaneous device may have means at the distal end of the extracorporeal portion 16 for attachment to an artificial leg (not shown).

Figure 2:
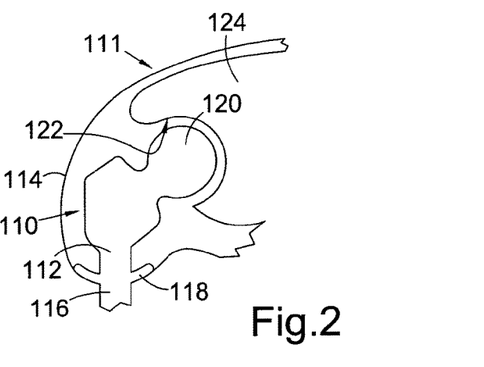
FIG. 2 shows a diagrammatic part cross-section through an embodiment of a percutaneous device for use in an anatomical shoulder disarticulation prosthesis, the device shown installed in a subject, the device having a ball component received in a subject's shoulder socket.

Referring to FIG. 2, this shows a percutaneous device 110, similar to the device 10 of FIG. 1, except that the device 110 of FIG. 2 is installed at the subject's 111 shoulder. Similar to the device of FIG. 1, the device of FIG. 2 has an intracorporeal or subcutaneous portion 112 which resides under the skin 114 when the device is installed, an extracorporeal portion 116 which extends from the skin when the device is installed, and a flange assembly 118 extending outwardly from the longitudinal axis of the intracorporeal portion 112. The device 110 has a ball component 120 at its proximal end when installed which is received in and articulates with the subject's natural shoulder socket (the glenoid fossa) 122 in the subject's scapula 124. Alternatively the ball component 120 may be received in and articulate with an artificial liner in the subject's glenoid socket, such as a prosthetic glenoid shell (not shown in the figures). The ball component is a substantially spherical, convex, articulating surface that is able to articulate with a subject's natural or prosthetic shoulder socket. The percutaneous device may have means at the distal end of the extracorporeal portion 116 for attachment to an artificial arm (not shown). All of the preferred features described in relation to the device of FIG. 1 may be applied in the device of FIG. 2 also.

Figure 3:
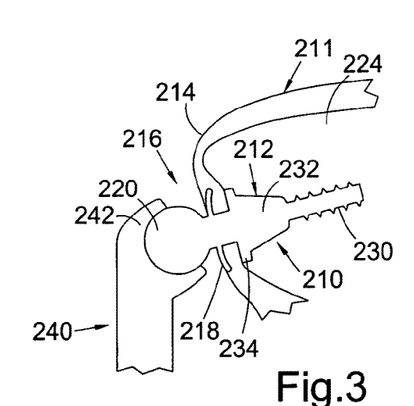
FIG. 3 shows a diagrammatic part cross-section through an embodiment of a percutaneous device for use in a reverse anatomical shoulder disarticulation prosthesis, the device shown installed in a subject, the device having a ball component that articulates with an exoprosthesis.

Referring to FIG. 3, this shows a percutaneous device 210 installed in a subject 211 at the shoulder. The percutaneous device 210 has an intracorporeal or subcutaneous portion 212 which resides under the skin 214 when the device is installed and an extracorporeal portion 216 which extends from the skin when the device is installed, and a flange assembly 218 extending outwardly from the longitudinal axis of the intracorporeal portion 212. Unlike the embodiment of FIG. 2, the percutaneous device 210 is used to provide a reverse anatomical shoulder prosthesis. In a reverse anatomical shoulder prosthesis the ball of the ball-and-socket shoulder joint is provided on a glenoid prosthesis component rather than on a humeral prosthesis component. In the embodiment of FIG. 3, the percutaneous device 210 comprises the glenoid prosthesis component of a prosthetic shoulder joint.

The extracorporeal portion 216 of the percutaneous device has a ball component 220 at its proximal end when installed, which is received in and articulates with a socket component 242 on the end of an exoprosthesis 240. The intracorporeal portion 212 of the percutaneous device has a threaded screw shank 230 at its proximal end, to engage into the bone of the glenoid cavity of the scapula 224. Between the screw threaded shank 230 and the extracorporeal portion 216 is a plate/shoulder 234 that is circular in plan centred on the axis of the screw thread shank 230 and with a transition from the plate portion 234 to the shank 230 that is a substantially frusto-conical form 232 tapering toward the shank 230. The plate/shoulder 234 may alternatively be ovoid in plan. The frustoconical transition 232 enables the device to be screw mounted to the glenoid surface to a substantial depth with a reduction in fragmentation of the exposed glenoid face by the screw threaded shank 230 and where the frustoconical surface 232 has a stabilising effect so that when forces are applied to the joint, the damage on the remaining glenoid bone is reduced. The frustoconical transition 232 is suitably coated with hydroxyapatite to encourage osseous integration and/or is micro-pitted.

In use, the ball component 220 of the percutaneous device is push-fitted or snap-fitted to the correspondingly shaped socket component 242 of the exoprosthesis 240. The exoprosthesis 240 may comprise an artificial arm or may comprise an extension component for attachment to an artificial arm.

Figure 4:
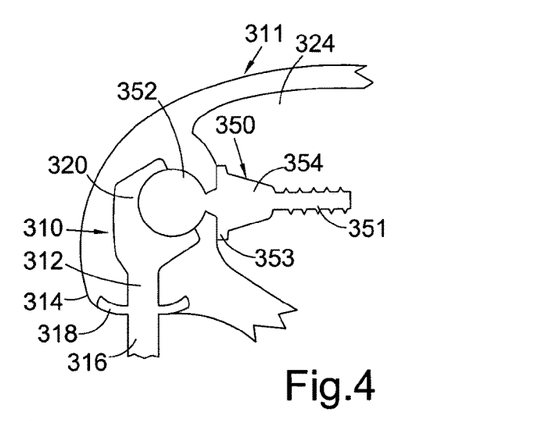
FIG. 4 shows a diagrammatic part cross-section through an embodiment of a percutaneous device for use in a reverse anatomical shoulder disarticulation prosthesis, the device shown installed in a subject, the device having a socket component that articulates with a bone-anchored endoprosthesis.

Referring to FIG. 4, this shows a percutaneous device 310 installed in a subject 311 at the shoulder. The percutaneous device 310 has an intracorporeal or subcutaneous portion 312 which resides under the skin 314 when the device is installed and an extracorporeal portion 316 which extends from the skin when the device is installed. The percutaneous device 310 of FIG. 4 is used to provide a reverse anatomical shoulder prosthesis. Unlike the embodiment of FIG. 3, the percutaneous device of FIG. 4 does not comprise a glenoid prosthesis component of a prosthetic shoulder joint. The percutaneous device of FIG. 4 has a socket component 320 at the proximal end of the intracorporeal portion in use, which couples to a separate glenoid prosthesis component 350. Extending outwardly from the intracorporeal portion 312 is a flange assembly 318, which provides a large surface area which advantageously facilitates the integration with fibrous tissue growth.

The glenoid prosthesis component 350 may be a Bayley-Walker® glenoid screw prosthesis or similar, as known and described in the prior art, for example in GB 2 405 346 (Stanmore Implants Worldwide Ltd). The glenoid prosthesis component 350 is anchored to the scapula 324 in use, the glenoid prosthesis component 350 having a threaded screw shank 351 to engage into the bone of the glenoid cavity and where the head part of the screw is formed as a ball 352 to co-operatively engage with the bearing surface of the socket component 320 of the percutaneous device.

Between the screw threaded shank 351 and the ball 352 of the glenoid prosthesis component 350 is an intermediate portion comprising a plate/shoulder 353 that is circular in plan centred on the axis of the screw thread shank 351 and with a transition from the plate portion 353 to the shank 351 that is a substantially frusto-conical form 354 tapering toward the shank 351. The plate/shoulder 234 may alternatively be ovoid in plan. This frustoconical transition 354 enables the glenoid prosthesis component 350 to be screw mounted to the glenoid surface to a substantial depth with a reduction in fragmentation of the exposed glenoid face by the screw threaded shank 351 and where the frustoconical surface 354 has a stabilising effect so that when forces are applied to the joint, the damage on the remaining glenoid bone is reduced. The frustoconical transition 354 is suitably coated with hydroxyapatite to encourage osseous integration and/or is micro-pitted.

In use, the ball 352 of the glenoid prosthesis component 350 may be push-fitted or snap-fitted to the correspondingly shaped socket component 320 of the percutaneous device 310.

In use, the percutaneous device 310 of FIG. 4 can pivot relative to the bone anchored glenoid prosthesis component, thereby providing means for coupling an external prosthesis to the subject.

It will be understood that the embodiment shown in FIGS. 3 and 4 could be used for a hip disarticulation.

Figure 5:
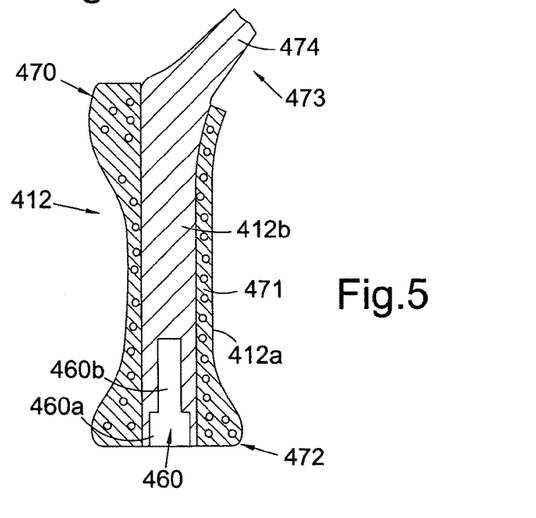
FIG. 5 shows a diagrammatic cross-section through an embodiment of a body component of the intracorporeal portion of a percutaneous device, similar to the FIG. 1 embodiment, for use in an anatomical hip disarticulation prosthesis; the device has a removable portion including the extracorporeal portion of the device, the removable portion not being present in the diagram.

Referring to FIG. 5, this shows a body component 412 of a percutaneous device 411 for use in an anatomical hip disarticulation prosthesis. The FIG. 5 embodiment is similar to the FIG. 1 embodiment, however in the FIG. 5 embodiment the extracorporeal portion is a separate piece from the main body of the intracorporeal portion. The body component 412 is an intracorporeal or subcutaneous portion of the device when installed. The body component has a bore or hole 460, for receiving a removable portion of the percutaneous device (not shown in FIG. 5). The bore 460 has a distal portion 460a when implanted, that is hexagonal in cross-section. The bore has a proximal portion 460b, adjoining the distal portion, the proximal portion being internally threaded (the internal threading not being visible in FIG. 5).

Figure 6A:
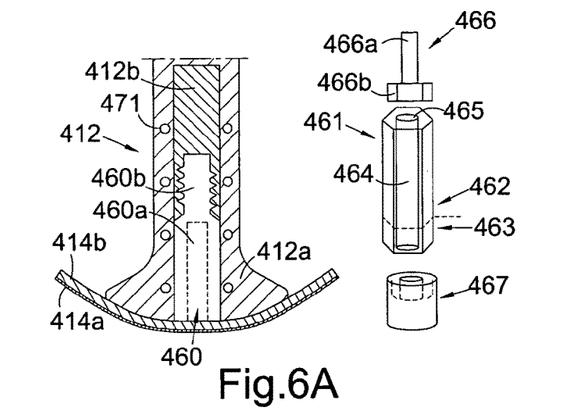
FIG. 6A shows an exploded diagrammatic cross-section through an embodiment of a body component of a percutaneous device, similar to the FIG. 5 embodiment, for use in an anatomical hip disarticulation prosthesis; the device has a removable portion including the extracorporeal portion of the device, the removable portion shown separate from the body component in the diagram.
Figure 6B:
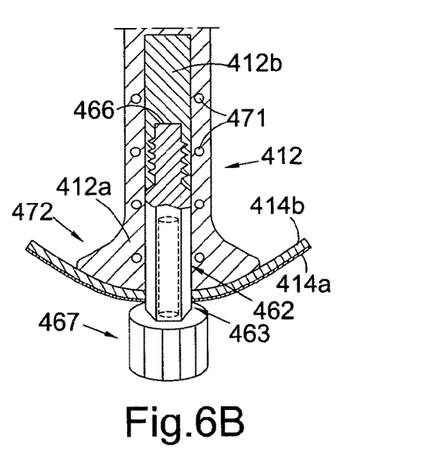
FIG. 6B shows a diagrammatic cross-section through the embodiment of FIG. 6A, but with the removable portion installed in the body component.

Referring to FIGS. 6A and 6B, the body component 412 is similar to the body component of FIG. 5, and common reference numerals are used in FIGS. 5, 6A and 6B for common features. Referring to FIGS. 6A and 6B, the removable portion 461 of the percutaneous device is shown. The removable portion 461 has an intracorporeal portion 462 which resides under the skin in use, which together with the body component 412, forms the intracorporeal portion of the percutaneous device when assembled and installed. The removable portion 461 also has an extracorporeal portion 463 which extends from the skin when the device is installed. The removable portion 461 comprises a hexagonal male component 464 that corresponds in shape to the hexagonal cross-section of the distal portion 460a of the bore 460 of the body component, such that the hexagonal male component 464 can be tightly received in the distal portion 460a of the bore. The hexagonal male component 464 has a central bore 465 along its longitudinal axis, in which a bolt 466 can be received. The bolt has a threaded shank 466a, which is threadedly receivable in the corresponding internally threaded proximal portion 460b of the bore 460 of the body component. The bolt has a head 466b which abuts an internal shoulder (not visible in the figures) of the hexagonal male component 464, such that the threaded shank 466a extends through the hole at the proximal end of the central bore 465 hexagonal male component 464. In use, to attach the removable portion 461 to the body component 412, the hexagonal male component 464 is inserted in the distal portion 460a of the bore of the body component, and the bolt 466 is inserted in the central bore 465 of the hexagonal male component 464; the bolt is threadedly engaged to the proximal portion 460b of the bore, to secure the removable portion 461 with the body component 412.

Other means for securably attaching the separate extracorporeal portion to the body component 412 of the device can be used. For example, the extracorporeal portion may have a male portion receivable in a female portion (e.g. a bore) in the body component 412, the bore having a cross-hole for access transversely to the region of the end of the male portion by a disassembly tool, similar to the cross-hole provided in the modular prosthesis disclosed in WO 02/47585 (Stanmore Implants Worldwide Limited).

An external spigot 467 may be attachable to the extracorporeal portion 463 of the hexagonal male component 464, the external spigot 467 being externally splined for use in attachment of an external prosthethetic device to the percutaneous device.

The removable portion 461 may be fitted to the body component 412 during initial surgery to install the body component in a subject. Alternatively the body component may be installed without the removable portion 461 inserted, the body component being fully covered over by the subject's skin and left for up to several months to allow tissue to integrate with it. During the integration period, when the body component is entirely residing within the subject's body, the bore 460 is filled with a plastic or metal fitting to prevent tissue ingrowth in the bore. Further surgery can then be performed to install the removable portion 461 in the body component 412, the plastic or metal filling in the bore 460 being removed during surgery prior to installation of the removable portion 461 in the bore 460. Once installed, the removable portion 461 extends through the patient's skin.

The intracorporeal body component 412 can be left in a patient indefinitely, without installation of the removable portion 461. In this way, the body component 412 can be used as a stump extender. The extended stump can be received in the socket of an exoprosthesis.

When installed, the hexagonal male component 464 cannot rotate relative to the body component 412, and the components are rigidly coupled to one another (i.e. non-movably coupled). Of course the distal portion 460a of the bore and the hexagonal male component 464 could have cross-sectional shapes other than hexagonal. If the male component 464 has a circular cross-section, it may include a lug engageable in a recess of the bore 460, to prevent rotation of the male component 464 with respect to the body component 412 when installed.

The body component 412 is preferably made of any suitable metal, such as titanium alloy or cobalt chrome. The body component 412 has regions wherein the body component body is porous and regions wherein the body component body is solid (i.e. non-porous). The porous regions may comprise a three dimensional porous network structure of pores. Such a body component can be manufactured using an Electron Beam Melting (EBM) machine (e.g. from Arcam AB). In the Electron Beam Melting process, an electron beam gun is used to selectively melt metal powder in a vacuum chamber to produce regions of solid metal and voids, arranged to create the desired size, shape, and pattern of holes in the distal and proximal portions of the body component. The body component 412 may have one or more 3D porous regions, with non-porous regions between. Alternatively, the body component may comprise regions of differing porosity. For example, the body component may have one or more regions of high porosity, one or more regions of lower porosity and optionally, one or more regions which are non-porous. Porosity is the ratio of the volume of pores to the total volume taken up by the material and pores. High porosity areas of the body component enhance tissue ingrowth (skin and/or muscle) with the body component. However, high porosity areas are weaker than low porosity/non-porous areas of a body component. Therefore, it is advantageous to have higher porosity regions combined with low/non-porous regions in the body component, to provide a body component which promotes tissue ingrowth, whilst retaining strength characteristics.

Referring to FIG. 5, the peripheral surface of the body component 212 surrounding its longitudinal axis comprises a porous region of material 412a, and the inner region 412b comprises a longitudinal core of solid metal for strength purposes. The body component 412 is shaped as a trochanter replacement component, shaped to correspond with an anatomical trochanter of the femur. The body component 412 has a greater trochanter portion 470 at its proximal end, shaped to correspond to an anatomical greater trochanter. The enlarged greater trochanter portion 470 of the body component is within the porous region 412a of the body component, such that there is a large surface area for attachment of residual muscle from the patient, in particular the abductor muscle. Between the distal and proximal ends of the body component 412 is a mid-portion of the body component, which has a substantially circular cross-sectional shape. The outer surface of the mid-portion of the body component 412 is porous to a depth of a few millimetres (preferably a depth of around 4 mm). The outer porous surface of the body component 412 provides a greater surface area for attachment of tissue. Preferably the pores of the porous regions have pore size diameter of around 350-700 microns. Most preferably, the average diameter of the apertures/pores is around 700 microns in diameter, as apertures/pores of this size have been found to enhance tissue ingrowth, since the apertures/pores are large enough not to restrict dermal invasion. The porous metal may be treated with a protein coating such as laminin or fibronectin to enhance cell attachment. The porous metal regions may be coated with hydroxyapatite (HA) using a plasma coating method or other line of site method. Additionally the inner pores may be coated with HA by a solution deposition method which may or may not involve electro deposition of a calcium phosphate material.

The outer surface region of the body component 412 includes a plurality of large holes 471, to promote muscle, tendon and/or fascia tissue attachment with the body component. Preferably the holes are through-holes, of the order of around 1 to 2 mm in diameter, and preferably around 2 mm in diameter. These macro-sized apertures/pores are large enough to allow a needle and polymer suture material (such as Fiberwire®)) to pass through, such that muscle can be secured to the body component using sutures. The sutures may be permanent or temporary. This promotes tissue integration following implantation. After implantation, over time, muscle tissue can ingrow through the macro-sized holes and also the micro-sized pores of the porous regions, further securing the body component to the nearby tissue. This then allows the subject to move the body component using their residual muscle, allowing the subject to pivot the body component about the subject's hip socket.

The distal end 472 of the body component 412 has a larger cross-sectional area than the mid-portion of the body component 412. The distal end 472 provides a flange, extending outwardly from the longitudinal axis of the body component 412. The distal end 472 lies under the epidermis 414a and the dermis 414b layers of the skin. As with the flange assemblies of the embodiments of FIGS. 1 to 4, the distal end 472 provides a large surface area for integration of skin and fibrous tissue with the body component. Referring to FIG. 6A, the distal surface of the distal end 472 is preferably convexly curved in shape, helping to prevent stresses being applied to the soft tissues that lie over the peripheral edge of the distal end when installed. Preferably, the flange shaped distal end 472 of the body component is porous to enhance attachment of skin tissue to the distal end; this prevents movement of the body component relative to the skin, helping the skin heal around the device and preventing epithelial downgrowth and infection. Dermal tissues may be attached to the distal end 472 by sutures which pass through 1-2 mm holes in the distal end 472 (not shown in the figures), similar to the holes 471.

If the intracorporeal body component 412 is installed in a patient without installation of the removable portion 461, to serve as a stump for supporting an exoprosthesis socket, in order to prevent spinning of the exoprosthesis socket the distal end 472 of the body component 412 may be non-circular in cross-sectional shape transverse to the direction of insertion to the body; the non-circular distal end resists rotation of the socket relative to the stump. For example, the flange or expanded distal part may be oval in shape. Alternatively, the flange or enlarged distal portion may be utilised adjacent to the subject's bone (but not as a stump extender) to provide rotational stability to a socket. In this case, the flange could be rigidly fixed to a residual bone (rather than coupled articulatingly with an intracorporeal joint component) using an intramedully stem or other suitable bone attachment means.

Typically, the body component will be around 100 mm in length from the distal end 472 to the proximal end of the greater trochanter portion 470. The diameter of the widened distal end 472 may be around 32 mm, with the distal bore portion 460a being around 12 mm in diameter.

Referring to FIG. 5, the body component 412 includes a femoral neck 473 with a trunion 474 to which a femoral head (not shown in FIG. 5) is attached in use.

Figures 7, 8, 9:
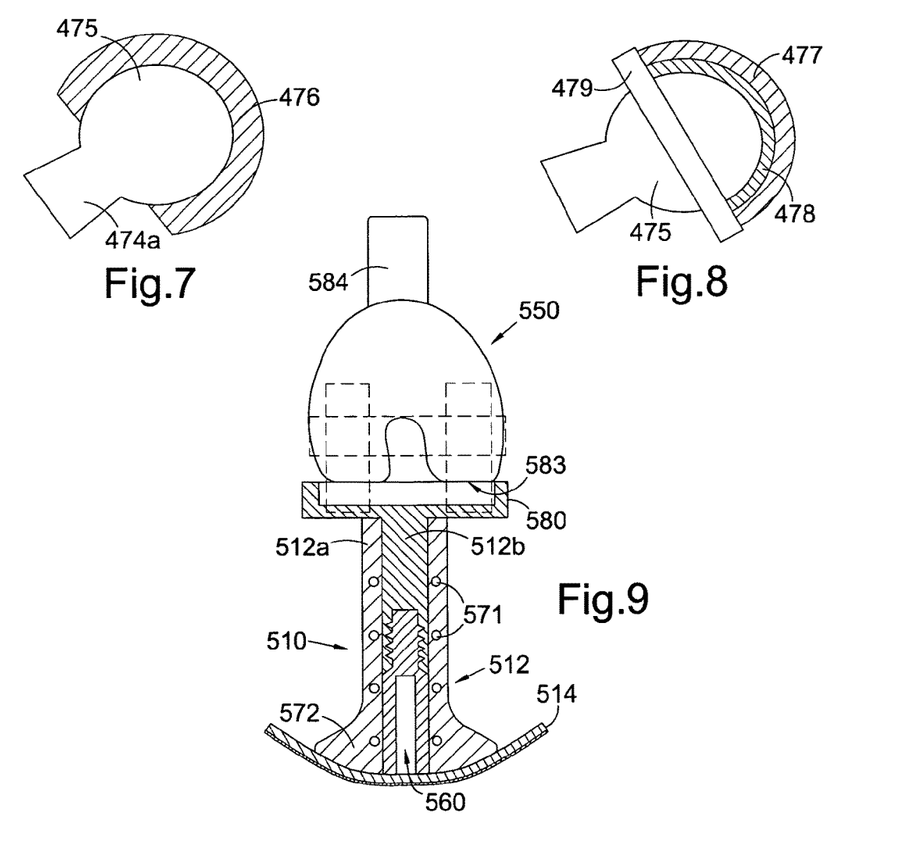
FIG. 7 shows a constrained femoral head inserted in prosthetic cup, the femoral head for attachment to the body component of FIG. 5 or 6A, and the prosthetic cup for installation in the subject's acetabulum.
FIG. 8 shows an alternative femoral head and prosthetic cup system to that of FIG. 7, the femoral head being held captive in the prosthetic cup by a ring attached to the prosthetic cup.
FIG. 9 shows a diagrammatic part cross-section through an embodiment of a percutaneous device for use in a joint replacement prosthesis for a patient having undergone a transfemoral amputation, the device shown installed in a subject, the device having a tibial component that articulates with an endoprosthesis.

FIGS. 7 and 8 show two possible types of femoral head and prosthetic cup assembly that can be used with the body component of FIGS. 5, 6A, 6B, or in the embodiments of FIGS. 1 and 2 (similar ball and socket systems could be used for the prosthetic humeral head and cup component of FIGS. 3 and 4). In each of the embodiments of FIGS. 7 and 8, there is a femoral head 475 having a corresponding trunion fitting 474a that fits onto the trunion 474 of the percutaneous device. Both the systems of FIGS. 7 and 8 are constrained ball and socket systems. Non-constrained systems rely on the downward force of the body through the joint and/or the tension created by the soft tissue, including muscles, ligaments and tendons to retain the prosthesis in its implanted position. Constrained systems include mechanisms for preventing dislocation of the components. FIG. 7 shows a femoral head 475 inserted in a prosthetic cup 476, and is a constrained cup system. The cup 476 has a greater than hemispherical coverage around the femoral head 475, such that the head is constrained within the internal diameter of the cup 476, thus preventing subluxation or dislocation of the head and cup. The femoral head 475 fits into the cup 476 via a snap-fit. The cup 476 is preferably made of polyethylene, more preferably ultra high molecular weight polyethylene. The cup 476 is implanted at the patient's acetabulum in use.

FIG. 8 shows an alternative constrained system. The system includes a metallic shell 477 that is implanted at the patient's acetabulum. The metallic shell 477 has a polyethylene bearing insert 478 that sits inside it, the liner 478 preferably being made of preferably ultra high molecular weight polyethylene. The femoral head 475 is inserted in the bearing insert 478 and a ring 479 is attached to the face of the metallic shell 477, constraining the head and preventing the head from dislocating. The ring 479 is preferably threadedly engaged to the metallic shell 477. The system of FIG. 8 may optionally omit the bearing insert 478, such that the femoral head bears directly against the metallic shell 477.

Referring to FIG. 9, this shows a percutaneous device 510, forming a joint replacement prosthesis, for installation in a subject that has had a transfemoral amputation. This shows a percutaneous device that can be used with a total joint replacement other than a shoulder or hip joint. The percutaneous device 510 has an intracorporeal portion 512 which resides under the skin 514 when the device is installed and an extracorporeal portion (not shown) which extends from the skin when the device is installed. The percutaneous device of FIG. 9 comprises a tibial component of a knee joint, having a tibial articulating component 580 at the proximal end of the intracorporeal portion in use, which articulates with a separate endoprosthesis 550 comprising a femoral knee hinge component having a condylar surface 583 for articulating with the tibial articulating component 580 of the percutaneous device 512. The proximal end of the endoprosthesis 550 includes a stem 584 for insertion into the intramedullary cavity of the patient's femur (not shown), to anchor the endoprosthesis 550 to the bone stump.

Like the FIG. 5, 6A, 6B embodiments, the intracorporeal portion 512 has a bore 560 for receiving a removeable portion (not shown) that includes a male portion for insertion in the bore 560 and an extracorporeal portion that extends from the intracorporeal portion and the skin when the removable portion is installed. As with the FIG. 5, 6A, 6B embodiments, the distal end 572 of the intracorporeal portion 512 has a larger cross-sectional area than the mid-portion of the intracorporeal portion. The distal end 572 provides a flange, extending outwardly from the longitudinal axis of the intracorporeal portion 512. As with the flange assemblies of the embodiments of FIGS. 1 to 4, the distal end 572 provides a large surface area for integration of skin and fibrous tissue with the intracorporeal portion. The distal surface of the distal end 572 is preferably convexly curved in shape, helping to prevent stresses being applied to the soft tissues that lie over the peripheral edge of the distal end when installed.

Like the body component of FIGS. 5, 6A and 6B, the intracorporeal portion 512 has a plurality of through-holes 571 passing through the body along it's peripheral edge. These allow muscle, tendon and fascia-tissue to attach to the device 512. Preferably the holes are around 2 mm in diameter, and are large enough to allow a needle to pass through, for securing tissue to the device 512. By securing tissue such as muscle, tendon and fascia-tissue attachment to the device 512, the subject can move the percutaneous device 512 using their residual muscle, allowing the percutaneous device 512 (the tibial component) to be pivoted relative to the femoral component 550. Like the body component of FIGS. 5, 6A and 6B, the intracorporeal portion 512 also has a core region 512b of solid metal for strength purposes and a porous region of material 512a surrounding the core 512b.

In use, the bore 560 receives a removable component (not shown) having an extracorporeal portion that extends from the skin in use. The extracorporeal portion of the removeable component has means for attaching an exoprosthesis to the extracorporeal portion. The rigid connection of the removable component (not shown in FIG. 9), having an extracorporeal portion, to the percutaneous device 512 allows the subject to directly move the extracorporeal portion of the percutaneous device using their muscle, and therefore to move an exoprosthesis secured to the extracorporeal portion of the percutaneous device.

It will be understood that the system of FIG. 9 could equally be applied to provide a total joint replacement for other joints, such as an elbow joint for a patient having undergone a transhumeral amputation. In such cases in the past, a patient would use an exoprosthesis having a socket for receiving the humeral stump and an exoprosthetic elbow joint, to secure the prosthesis to the stump. The advantage of a percutaneous device according to the invention for use in a joint replacement is that the joint is contained within the patient's body, and is not part of an exoprosthesis. By integration of the muscle, fascia tissue and tendons with the percutaneous device, the patient can have direct control over the replacement joint using their residual muscle, rather than relying on body control or myoelectric control of an exoprosthetic joint that would be required The percutaneous devices of the various embodiments of the invention are preferably made of titanium, titanium alloy or cobalt chrome, in order to provide the percutaneous prosthesis with high strength characteristics. It is important that the percutaneous prosthesis will not be liable to bend or break when the extracorporeal portion is subjected to large forces, therefore the percutaneous prosthesis must comprise a strong, rigid structure. The extracorporeal portion of the percutaneous device may include a safety device comprising linkage which breaks under an unusual load such as, for example, one caused by the patient falling. This will allow the extracorporeal portion to detach from the intracorporeal portion without causing damage to the skin (or bone, if the percutaneous device is bone anchored).

For the embodiment of FIG. 3, in which the percutaneous device 210 is bone anchored, the threaded shank 230 may be substituted with other suitable attachment means for securing the device to the scapula. In the embodiment of FIG. 4, in which a glenoid prosthesis component 350 is bone anchored, the threaded shank 351 may be substituted with other suitable attachment means for securing the component to the scapula.

In the various embodiments, the intracorporeal portion of the percutaneous device may be given a surface treatment to encourage muscle or dermal integration with the device. Such surface treatments include giving the surface a micro-pitted structure and/or coating the surface with adhesion proteins such as laminin or fibronectin which encourage fibrous growth into the surface of the device. A surface is provided on the intracorporeal portion which is porous and promotes fibrous tissue ingrowth. Suitable materials for coating the surface include alumina oxide ceramics or hydroxyapatite. This surface, preferably after being given a porous surface treatment, is coated with an adhesion promoting protein, e.g. by spraying the prosthesis with a solution of the adhesion-promoting protein, by dipping the prosthesis in a concentrated solution of the protein and freeze drying, or by dipping into a sterile solution of the adhesion-promoting protein prior to installation.

In the embodiments of FIGS. 1-8, the surface of the ball component 20, 120, 220, 475 of the percutaneous device will preferably have a surface of low-friction material, such as ultra-high molecular weight polyethylene (UHMWPE), to provide a suitable bearing surface for articulating with the corresponding socket. In the embodiment of FIG. 4, the surface of the ball component 352 of the glenoid prosthesis component 350 will preferably have a surface of low-friction material, such as ultra-high molecular weight polyethylene (UHMWPE), to provide a suitable bearing surface for articulating with the corresponding socket. In the embodiment of FIG. 4, the articulating surface of the socket component 320 of the percutaneous device will also preferably have a surface of low-friction material, such as ultra-high molecular weight polyethylene (UHMWPE), to provide a suitable bearing surface for articulating with the corresponding ball.

Prior to installing the percutaneous device, the hypodermis is preferably surgically removed. The removal of the hypodermis surgically during the amputation and installation procedure assists in stimulating attachment of the skin to the device and thereby prevents shear forces on the skin separating the epithelial cells at the interface.

In the various embodiments, the extracorporeal portion of the percutaneous device that extends from the skin surface may be given a non-stick surface on its exterior portion. Suitable materials include fluorinated polymers such as polytetrafluoroethylene, siliconised polymers and diamond-like carbon. Alternatively the outer surface of the extracorporeal portion may be polished to provide a non-stick, low surface energy outer surface. The presence of a non-stick surface discourages bacteria from attaching to the prosthesis and helps to prevent infection. The non-stick surface may be applied to the exterior of the extracorporeal portion using the technique of chemical vapour deposition (CVD). The use of CVD is well known in the art for applying a surface of diamond-like carbon. When applying a surface layer of diamond, as disclosed in EP B-0545 542 the method generally involves providing a mixture of hydrogen or oxygen gas and a suitable gaseous carbon compound such as a hydrocarbon, applying energy to that gas to dissociate the hydrogen into atomic hydrogen or the oxygen into atomic oxygen and the carbon into active carbon ions, atoms or CH radicals and allowing such active species to deposit on the substrate to form diamond. The energy to cause dissociation may be provided in a number of ways common to the art, for example by hot filament or by microwave source. A non-stick surface fluorinated polymer or silicone polymer may be applied to the extracorporeal portion of the percutaneous device by polymerising a monomer or prepolymer in contact with the component.

It may be convenient to apply the low energy surface treatment to the extracorporeal portion while masking the remaining components of the prosthesis. Also, the intracorporeal portion of the prosthesis may be treated with the adhesion-promoting protein after applying the low energy surface to the extracorporeal portion, and it may be desirable to mask the extracorporeal portion while applying the adhesion-promoting protein.

The flange assembly 18, 118, 218, 318 and distal end 472, 572 of the percutaneous devices of the figures may have through-holes, through which dermal and/or muscle tissue can integrate. The flange assembly/distal end may have surface treatments to encourage muscle or dermal integration with the device. Such surface treatments include giving the surface a micro-pitted structure and/or coating the surface with adhesion proteins such as laminin or fibronectin which encourage fibrous growth into the surface or with alumina oxide ceramics and hydroxyapatite. The flange assembly/distal end may be different shapes. Alternatively, the percutaneous device may have no flange assembly.

Each of the devices described may be provided as a single piece or provided as a set comprising modular components that are assembled together.

The device may be provided as a modular kit, wherein components of the device are provided separately and are connected together, some of the components being provided optionally in different sizes and/or with attributes such as different surface coatings, or in different shapes or sizes. For example, the intracorporeal portion of the device may be provided with a removable ball or socket component in different sizes, for providing a prosthesis for anatomical or reverse anatomical ball-and-socket joint replacement as shown in FIGS. 2 and 4 respectively.

Where an artificial limb is connected to the percutaneous device of any of the above described embodiments, the artificial limb may simply be a cosmetic/passive limb to restore the subject's anatomical shape. Alternatively the artificial limb may be controlled using control systems known in the prior art. For example, the artificial limb may be controlled by the subject's own body power, such as using cable-activation, or the artificial limb may incorporate a power source to activate the prosthesis using myoelectric control.

The invention claimed is:

1. A method of installing a percutaneous device which comprises an intracorporeal portion configured to be located within a subject's body and an extracorporeal portion configured to be located exterior to skin of the subject, the intracorporeal portion having an articulating component for articulating with an articulating surface, the method comprising implanting the percutaneous device such that the intracorporeal portion is under the subject's skin and at least a portion of the extracorporeal portion is located exterior to the skin such that the percutaneous device passes through the skin when installed and coupling the articulating component with the articulating surface of the subject such that the articulating component can articulate with the articulating surface in use.

2. A method according to claim 1, wherein the intracorporeal portion and extracorporeal portion are initially separate pieces and the method of installing the percutaneous device includes rigidly coupling the extracorporeal portion to the intracorporeal portion.

3. A method according to claim 2, wherein the extracorporeal portion has a male pin and the intracorporeal portion has a corresponding female socket, the coupling of the extracorporeal portion to the intracorporeal portion including the step of inserting the male pin of the extracorporeal portion into the female socket of the intracorporeal portion.

4. A method according to claim 1, wherein the intracorporeal portion and extracorporeal portion are integral with one another.

5. A method according to claim 1, wherein the articulating component is integral with the intracorporeal portion.

6. A method according to claim 1, wherein the articulating component is rigidly coupled to the intracorporeal portion before the percutaneous device is installed.

7. A method according to claim 1, wherein the step of coupling the articulating component with the articulating surface of the subject includes coupling the articulating component with a natural articulating surface of a subject's joint.

8. A method according to claim 1, wherein the step of coupling the articulating component with the articulating surface of the subject includes coupling the articulating component with a prosthetic articulating surface installed at a subject's joint.

9. A method according to claim 1, wherein the articulating component comprises a ball component and the step of coupling the articulating component with the articulating surface of the subject includes coupling the ball component with a socket of a ball and socket joint.

10. A method according to claim 1, wherein the articulating component comprises a ball component and the step of coupling the articulating component with the articulating surface of the subject includes coupling the ball component with a hip socket or shoulder socket of a subject.

11. A method according to claim 1, wherein the articulating component comprises a ball component and the step of coupling the articulating component with the articulating surface of the subject includes coupling the ball component with a prosthetic bearing surface installed in a hip socket or shoulder socket.

12. A method according to claim 1, wherein the articulating component comprises a socket component and the step of coupling the articulating component with the articulating surface of the subject includes coupling the socket component with a ball component of a bone anchored endoprosthesis.

13. A method according to claim 1, wherein the articulating component comprises a tibial component and the step of coupling the articulating component with the articulating surface of the subject includes coupling the tibial component with a condylar surface of a subject's knee joint.

14. A method according to claim 1, wherein the articulating component comprises a tibial component and the step of coupling the articulating component with the articulating surface of the subject includes coupling the tibial component with a femoral hinge component of a knee endoprosthesis.

15. A method according to claim 1, wherein at least a portion of the intracorporeal portion is treated to promote cutaneous integration.

16. A method according to claim 1, wherein at least a portion of the intracorporeal portion has a surface coating to promote cutaneous integration.

17. A method according to claim 1, wherein at least a portion of the intracorporeal portion is porous.

18. A method according to claim 1, wherein the intracorporeal portion further comprises a flange extending outwardly from the intracorporeal portion.

19. A method according to claim 1, wherein the intracorporeal portion has a plurality of apertures for attaching the subject's soft tissue to the intracorporeal portion.

* * * * *